US007482492B2

(12) United States Patent
Coggan et al.

(10) Patent No.: US 7,482,492 B2
(45) Date of Patent: *Jan. 27, 2009

(54) COST EFFECTIVE METHOD FOR SYNTHESIS OF TRIARYLAMINE COMPOUNDS

(75) Inventors: Jennifer A. Coggan, Cambridge (CA); Nan-Xing Hu, Oakville (CA)

(73) Assignee: Xerox Corporation, Norwalk, CT (US)

( * ) Notice: Subject to any disclaimer, the term of this patent is extended or adjusted under 35 U.S.C. 154(b) by 144 days.

This patent is subject to a terminal disclaimer.

(21) Appl. No.: 11/734,593

(22) Filed: Apr. 12, 2007

(65) Prior Publication Data

US 2008/0255389 A1 Oct. 16, 2008

(51) Int. Cl.
*C07C 209/10* (2006.01)

(52) U.S. Cl. .................. 564/405; 564/305; 564/399

(58) Field of Classification Search ................ 564/399, 564/405
See application file for complete search history.

(56) References Cited

U.S. PATENT DOCUMENTS

| 3,121,006 | A | 2/1964 | Middleton et al. |
| 4,265,990 | A | 5/1981 | Stolka et al. |
| 4,286,033 | A | 8/1981 | Neyhart et al. |
| 4,291,110 | A | 9/1981 | Lee |
| 4,338,387 | A | 7/1982 | Hewitt |
| 4,457,994 | A | 7/1984 | Pai et al. |
| 4,654,284 | A | 3/1987 | Yu et al. |
| 4,871,634 | A | 10/1989 | Limburg et al. |
| 5,368,967 | A | 11/1994 | Schank et al. |
| 5,418,107 | A | 5/1995 | Nealey et al. |
| 5,648,542 | A | 7/1997 | Goodbrand et al. |
| 5,654,482 | A | 8/1997 | Goodbrand et al. |
| 5,702,854 | A | 12/1997 | Schank et al. |
| 5,705,697 | A | 1/1998 | Goodbrand et al. |
| 5,709,974 | A | 1/1998 | Yuh et al. |
| 5,723,669 | A | 3/1998 | Goodbrand et al. |
| 5,723,671 | A | 3/1998 | Goodbrand et al. |
| 5,902,901 | A | 5/1999 | Goodbrand et al. |
| 5,976,744 | A | 11/1999 | Fuller et al. |
| 6,894,191 | B1 * | 5/2005 | Kelkar et al. ................. 564/405 |
| 7,138,555 | B2 | 11/2006 | Goodbrand et al. |
| 7,196,214 | B2 | 3/2007 | Goodbrand et al. |
| 7,345,203 | B1 * | 3/2008 | Bender et al. ............... 564/407 |
| 2006/0111583 | A1 | 5/2006 | Bender et al. |
| 2006/0111588 | A1 | 5/2006 | Bender et al. |
| 2006/0115755 | A1 | 6/2006 | Bender et al. |
| 2006/0160002 | A1 | 7/2006 | Qi et al. |
| 2006/0222977 | A1 | 10/2006 | Goodbrand et al. |

OTHER PUBLICATIONS

U.S. Appl. No. 11/260,249, filed Oct. 28, 2005, to Qi et al.
U.S. Appl. No. 11/263,671, filed Nov. 1, 2005, to Coggan et al.
U.S. Appl. No. 11/563,873, filed Nov. 28, 2006, to Bender et al.
U.S. Appl. No. 11/563,931, filed Nov. 28, 2006, to Bender et al.
U.S. Appl. No. 11/563,937, filed Nov. 28, 2006, to Bender et al.

* cited by examiner

*Primary Examiner*—Brian J Davis
(74) *Attorney, Agent, or Firm*—Oliff & Berridge, PLC (57) ABSTRACT

A process for forming a triarylamine compound includes reacting a halogenated aryl alcohol with an alcohol protecting agent and a first base to form a halogenated protected aryl alcohol compound, and reacting the halogenated protected aryl alcohol compound with an amine in the presence of a suitable catalyst and a second base.

27 Claims, 3 Drawing Sheets

COST EFFECTIVE METHOD FOR SYNTHESIS OF TRIARYLAMINE COMPOUNDS

TECHNICAL FIELD

This disclosure is generally directed to improved chemical processes for the synthesis of arylamine compounds, and to the use of such arylamine compounds in producing charge transport layers and overcoating layers for electrophotographic imaging members. In particular, this disclosure provides a two-step method for producing a triarylamine molecule directly by the reaction of a mono- or di-aryl amine (such as an aniline or a diarylamine) with a halogenated aryl alcohol, using a halogenated protected aryl alcohol compound as an intermediate.

RELATED APPLICATIONS

Commonly assigned, U.S. patent application Ser. No. 11/563,931 filed Nov. 28, 2006, describes a process for forming a triarylamine compound, comprising reacting an aniline and an arylchloride in the presence of a palladium ligated catalyst and a base.

Commonly assigned, U.S. patent application Ser. No. 11/563,873 filed Nov. 28, 2006, describes a process for forming a diarylamine compound, comprising reacting an aniline and an arylbromide in the presence of a palladium ligated catalyst and a base.

Commonly assigned, U.S. patent application Ser. No. 11/563,937 filed Nov. 28, 2006, describes an improved method for the preparation of derivatives of 4-aminobiphenyl using a ligated palladium catalyst in the presence of base.

Commonly assigned. U.S. patent application Ser. No. 11/263,671 filed Nov. 1, 2005, describes a process for the preparation of a tertiary arylamine compound, comprising reacting an arylhalide and an arylamine in an ionic liquid in the presence of a catalyst.

Commonly assigned, U.S. patent application Ser. No. 10/992,690 filed Nov. 22, 2004, describes a process for forming a tertiary arylamine compound, comprising reacting an arylbromide and an arylamine. For example, the application describes a process for forming N,N-diphenyl-4-aminobiphenyl, comprising reacting 4-bromobiphenyl and diphenylamine in the presence of a palladium-ligated catalyst.

Commonly assigned, U.S. patent application Ser. No. 10/992,687 filed Nov. 22, 2004, describes a process for forming a 4-aminobiphenyl derivative arylamine compound, comprising: (i) providing a first disubstituted 4-aminobiphenyl compound; (ii) optionally formylating the first disubstituted 4-aminobiphenyl compound to form a bisformyl substituted compound, where the first disubstituted 4-aminobiphenyl compound is not a bisformyl substituted compound; (iii) acidifying the bisformyl substituted compound to convert formyl functional groups into acid functional groups to form an acidified compound; and (iv) hydrogenating the acidified compound to saturate at least one unsaturated double bonds in the acidified compound, wherein there is provided a second disubstituted 4-aminobiphenyl compound.

Commonly assigned, U.S. patent application Ser. No. 10/992,658 filed Nov. 22, 2004, describes a process for forming a 4-aminobiphenyl derivative arylamine compound, comprising: (i) providing an iodinated organic compound; (ii) substituting the iodinated organic compound at carboxylic acid groups thereof to provide ester protecting groups; (iii) conducting an Ullman condensation reaction to convert the product of step (ii) into an arylamine compound; and (iv) conducting a Suzuki coupling reaction to add an additional phenyl group to the arylamine compound in the 4-position relative to the nitrogen, to provide the 4-aminobiphenyl derivative arylamine compound.

Commonly assigned, U.S. patent application Ser. No. 11/094,683 filed Mar. 31, 2005, describes a process for forming an anhydrous alkali earth salt of a dicarboxylic acid of an arylamine compound, comprising reacting, a dicarboxylic acid of an arylamine compound with an anhydrous alkali earth salt. The application also discloses a process for forming a siloxane-containing hole-transport molecule, comprising: reacting a dicarboxylic acid of an arylamine compound with an anhydrous alkali earth salt to form an anhydrous dicarboxylic acid salt of the arylamine compound; and reacting the anhydrous dicarboxylic acid salt of the arylamine compound with a siloxane-containing compound.

Commonly assigned, U.S. patent application Ser. No. 10/998,585 filed Nov. 30, 2004, describes a silicon-containing layer for electrophotographic photoreceptors comprising: one or more siloxane-containing compound; and one or more siloxane-containing antioxidant; wherein the siloxane-containing antioxidant is at least one member selected from the group consisting of hindered-phenol antioxidants, hindered-amine antioxidants, thioether antioxidants and phosphite antioxidants.

Commonly assigned, U.S. patent application Ser. No. 11/034,713 filed Jan. 14, 2005, describes an electrophotographic photoreceptor comprising a charge-generating layer, a charge-transport layer, and an overcoat layer comprised of a crosslinked siloxane composite composition comprising at least one siloxane-containing compound and metal oxide particles.

Commonly assigned. U.S. patent application Ser. No. 10/709,193 filed Apr. 20, 2004, describes a process for preparing an aryl iodide compound, comprising: reacting an aryl halide compound with a metal iodide, a metal catalyst and a catalyst coordinating ligand in at least one solvent to form an aryl iodide; and purifying the aryl iodide; wherein the solvent is heated to reflux during the reacting; wherein an aryl iodide yield of at least about 75% is obtained; and wherein the aryl iodide has a purity of at least 90%.

Commonly assigned, U.S. patent application Ser. No. 11/260,249 filed Oct. 28, 2005, describes a photoconductive member comprising: a charge generating layer; a charge transport layer; and a layer in contact with the charge transport layer comprising a substantially crosslinked resin of at least a phenol compound and a charge transport compound, wherein the charge transport compound is represented by $A_1\text{-}(L.\text{-}OR)_n$ wherein A represents a charge transport component, L represents a linkage group, O represents oxygen, R represents a hydrocarbyl group, and n represents a number of repeating segments or groups.

The appropriate components and process aspects of each of the foregoing, such as the arylamine precursor materials and electrophotographic imaging members, may be selected for the present disclosure in embodiments thereof. The entire disclosures of the above-mentioned applications are totally incorporated herein by reference.

REFERENCES

Various overcoats employing alcohol soluble polyamides have been proposed. Disclosed in U.S. Pat. No. 5,368,967 is an electrophotographic imaging member comprising a substrate, a charge generating layer, a charge transport layer, and an overcoat layer comprising a small molecule hole transporting arylamine having at least two hydroxy functional groups, a hydroxy or multihydroxy triphenyl methane, and a polyamide film forming binder capable of forming hydrogen bonds with the hydroxy functional groups such as the hydroxy arylamine and hydroxy or multihydroxy triphenyl methane. This overcoat layer may be fabricated using an alcohol solvent. This electrophotographic imaging member may be used in an electrophotographic imaging process. Specific materials including ELVAMIDE® polyamide, N,N'-diphenyl-N,N'-bis (3-hydroxyphenyl)-(1,1'-biphenyl)-4,4'-diamine and bis-[2-methyl-4-(N-2'-hydroxyethyl-N-ethyl-aminophenyl)]-phenylmethane are disclosed in this patent.

A crosslinked polyamide overcoat is known, comprising a crosslinked polyamide containing N,N'-diphenyl-N,N'-bis(3-hydroxyphenyl)-(1,1'-biphenyl)-4,4'-diamine, and referred to as LUCKAMIDE®. In order to achieve crosslinking, a polyamide polymer having N-methoxymethyl groups (LUCKAMIDE®) was employed along with a catalyst such as oxalic acid. This overcoat is described in U.S. Pat. No. 5,702,854, the entire disclosure thereof being incorporated herein by reference.

Disclosed in U.S. Pat. No. 5,976,744 is an electrophotographic imaging member including a supporting substrate coated with at least one photoconductive layer, and an overcoating layer. The overcoating layer includes hydroxy functionalized aromatic diamine and a hydroxy functionalized triarylamine dissolved or molecularly dispersed in a crosslinked acrylated polyamide matrix. The hydroxy functionalized triarylamine is a compound different from the polyhydroxy functionalized aromatic diamine.

Disclosed in U.S. Pat. No. 5,709.974 is an electrophotographic imaging member including a charge generating layer, a charge transport layer and an overcoating layer. The transport layer includes a charge transporting aromatic diamine molecule in a polystrene matrix. The overcoating layer includes a hole transporting hydroxy arylamine compound having at least two hydroxy functional groups, and a polyamide film forming binder capable of forming hydrogen bonds with the hydroxy functional groups of the hydroxy arylamine compound.

Disclosed in U.S. Pat. No. 5,368,967 is an electrophotographic imaging member comprising a substrate, a charge generating layer, a charge transport layer, and an overcoat layer comprising a small molecule hole transporting arylamine having at least two hydroxy functional groups, a hydroxy or multihydroxy triphenyl methane, and a polyamide film forming binder capable of forming hydrogen bonds with the hydroxy functional groups such as the hydroxy arylamine and hydroxy or multihydroxy triphenyl methane. This overcoat layer may be fabricated using an alcohol solvent. This electrophotographic imaging member may be used in an electrophotographic imaging process. Specific materials including ELVAMIDE® polyamide and N,N'-diphenyl-N,N'-bis(3-hydroxyphenyl)-(1,1'-biphenyl)-4,4'-diamine and bis-[2-methyl-4-(N-2-hydroxyethyl-N-ethyl-aminophenyl)]-phenyl methane are disclosed in this patent.

Disclosed in U.S. Pat. No. 4,871,634 is an electrostatographic imaging member containing at least one electrophotoconductive layer. The imaging member comprises a photogenerating material and a hydroxy arylamine compound represented by a certain formula. The hydroxy arylamine compound can be used in an overcoat with the hydroxy arylamine compound bonded to a resin capable of hydrogen bonding such as a polyamide possessing alcohol solubility.

Disclosed in U.S. Pat. No. 4,457,994 is a layered photosensitive member comprising a generator layer and a transport layer containing a diamine type molecule dispersed in a polymeric binder, and an overcoat containing triphenyl methane molecules dispersed in a polymeric binder.

Disclosed in U.S. Pat. No. 5,418,107 is a process for fabricating an electrophotographic imaging member.

The disclosures of each of the foregoing patents and publications, and the disclosures of any patents and publications cited below, are hereby totally incorporated by reference. The appropriate components and process aspects of the each of the foregoing patents and publications may also be selected for the present compositions and processes in embodiments thereof.

BACKGROUND

In electrophotography, an electrophotographic substrate containing a photoconductive insulating layer on a conductive layer is imaged by first uniformly electrostatically charging a surface of the substrate. The substrate is then exposed to a pattern of activating electromagnetic radiation, such as, for example, light. The electromagnetic radiation selectively dissipates charge in illuminated areas of the photoconductive insulating layer while leaving behind an electrostatic latent image in non-illuminated areas of the photoconductive insulating layer. This electrostatic latent image is then developed to form a visible image by depositing finely divided electroscopic marking particles on the surface of the photoconductive insulating layer. The resulting visible image is then transferred from the electrophotographic substrate to a necessary member, such as, for example, an intermediate-transfer member or a print substrate, such as paper. This image developing process can be repeated as many times as necessary with reusable photoconductive insulating layers.

In image-forming apparatus such as copiers, printers, and facsimiles, electrophotographic systems in which charging, exposure, development, transfer, etc., are carried out using electrophotographic photoreceptors have been widely employed. In such image-forming apparatus, there are ever-increasing demands for speeding up of image-formation processes, improvement in image quality, miniaturization and prolonged life of the apparatus, reduction in production cost and running cost, etc. Further, with recent advances in computers and communication technology, digital systems and color-image output systems have been applied also to the image-forming apparatus.

Electrophotographic imaging members (such as photoreceptors) are known. Electrophotographic imaging members are commonly used in electrophotographic processes having either a flexible belt or a rigid drum configuration. These electrophotographic imaging members sometimes comprise a photoconductive layer including a single layer or composite layers. These electrophotographic imaging members take many different forms. For example, layered photoresponsive imaging members are known in the art. U.S. Pat. No. 4,265, 990 to Stolka et al. describes a layered photoreceptor having separate photogenerating and charge-transport layers. The photogenerating layer disclosed in Stolka is capable of photogenerating holes and injecting the photogenerated boles into the charge-transport layer. Thus, in the photoreceptors of Stolka, the photogenerating material generates electrons and holes when subjected to light.

More advanced photoconductive photoreceptors containing highly specialized component layers are also known. For example, a multi-layered photoreceptor employed in electrophotographic imaging systems sometimes includes one or more of a substrate, an undercoating layer, an intermediate layer, an optional hole- or charge-blocking layer, a charge-generating layer (including a photogenerating material in a binder) over an undercoating layer and/or a blocking layer, and a charge-transport layer (including a charge-transport material in a binder). Additional layers such as one or more overcoat layer or layers are also sometimes included.

In view of such a background, improvement in electrophotograpic properties and durability, miniaturization, reduction in cost, and the like, in electro-photographic photoreceptors have been studied, and electrophotographic photoreceptors using various materials have been proposed.

Production of a number of arylamine compounds, such as arylamine compounds that are useful as charge-transport compounds in electrostatographic imaging devices and processes, often involves synthesis of intermediate materials, some of which generally are costly and/or time-consuming to produce, and some of which involve a multi-step process.

One such class of compounds are triarylamines. Certain triarylamine compounds may be produced by reaction of an aniline with an aryliodide under traditional Ullman conditions (copper catalyst, high temperature, long reaction time) or the so-called ligand-accelerated Ullman reaction that uses lower reaction temperatures but is still limited to the use of aryliodides (see Goodbrand et al: U.S. Pat. Nos. 5,902,901; 5,723,671; 5,723,669; 5,705,697; 5,654,482; and 5,648,542). Aryliodides tend to be very expensive reagents. Furthermore, both of these reactions usually require lengthy and costly purification processes.

Further, such reactions that start with an Ullman reaction are often followed by multi-step reaction processes that use dangerous or reactive reagents or catalysts, and often involve dangerous reduction processes. For example, typical reaction schemes for producing triarylamines utilize Vilsmeier reagents such as $POCl_3$ or $POBr_3$ that are very corrosive, and/or use hydrogen reduction reactions that can be very dangerous. These drawbacks, while nominal in a laboratory scale, pose significant challenges in scaling up a reaction to commercial level.

Accordingly, improved processes providing safe, cost-effective, and efficient methods for triarylamine production are desired.

SUMMARY

The present disclosure addresses these and other needs, by providing an improved method for the preparation of triarylamines. More particularly, this disclosure provides an improved method of producing triarylamine compounds having one or more alkoxy groups by the reaction of a mono- or di-aryl amine (such as an aniline or a diaryl amine) with a halogenated aryl alcohol. The reaction is generally a two-step process, where the halogenated aryl alcohol is first protected to form a halogenated protected aryl alcohol compound, followed by a second step of reacting the halogenated protected aryl alcohol compound with an amine, such as a mono- or di-aryl amine.

In embodiments, the disclosure provides a process for forming a triarylamine compound, comprising:

(1) reacting a halogenated aryl alcohol with an alcohol protecting agent and a first base to form a halogenated protected aryl alcohol compound, and (2) reacting the halogenated protected aryl alcohol compound with an amine in the presence of a suitable catalyst and a second base.

EMBODIMENTS

This disclosure is not limited to particular embodiments described herein, and some components and processes may be varied by one of skill, based on this disclosure. The terminology used herein is for the purpose of describing particular embodiments only, and is not intended to be limiting.

In this specification and the claims that follow, singular forms such as "a," "an," and "the" include plural forms unless the content clearly dictates otherwise. In addition, reference may be made to a number of terms that shall be defined as follows:

The terms "hydrocarbon" and "alkane" refer, for example, to branched and unbranched molecules having the general formula $C_nH_{2n+2}$, wherein n is, for example, a number from 1 to about 100 or more, such as methane, ethane, n-propane, isopropane, n-butane, isobutane, tert-butane, octane, decane, tetradecane, hexadecane, eicosane, tetracosane, and the like. Alkanes may be substituted by replacing hydrogen atoms with one or more functional groups. The term "aliphatic" refers, for example, to straight-chain molecules, and may be used to describe acyclic, unbranched alkanes. The term "long-chain" refers, for example, to hydrocarbon chains in which n is a number of from about 8 to about 60, such as from about 20 to about 45 or from about 30 to about 40. The term "short-chain" refers, for example, to hydrocarbon chains in which n is an integer of from about 1 to about 7, such as from about 2 to about 5 or from about 3 to about 4.

The term "alkyl" refers, for example, to a branched or unbranched saturated hydrocarbon group, derived from an alkane and having the general formula $C_nH_{2n+1}$, wherein n is, for example, a number from 1 to about 100 or more, such as methyl, ethyl, n-propyl, isopropyl, n-butyl, isobutyl, tert-butyl, octyl, decyl, tetradecyl, hexadecyl, eicosyl, tetracosyl, and the like. The term "lower alkyl" refers, for example, to an alkyl group of from about 1 to about 12 carbon atoms. "Halogenated alkyl" refers, for example, to an alkyl group in which at least one hydrogen atom, and optionally all hydrogen atoms, is replaced by a halogen atom.

The term "aryl" refers, for example to a monocyclic aromatic species of about 6 to about 20 carbon atoms or more, such as phenyl, naphthyl, anthrycyl, and the like. Optionally, these groups may be substituted with one or more independently selected substituents, including alkyl, alkenyl, alkoxy, hydroxyl and nitro groups.

The term "arylamine" refers, for example, to moieties containing both aryl and amine groups. Exemplary aralkylene groups have the structure Ar—NRR', in which Ar represents an aryl group and R and R' are groups that may be independently selected from hydrogen and substituted and unsubstituted alkyl, alkenyl, aryl, and other suitable functional groups. The term "triarylamine" refers, for example, to arylamine compounds having the general structure NArAr'Ar", in which Ar, Ar' and Ar" represent independently selected aryl groups.

The term "organic molecule" refers, for example, to any molecule that is made up predominantly of carbon and hydrogen, such as, for example, alkanes and arylamines. The term "heteroatom" refers, for example, to any atom other than carbon and hydrogen. Typical heteroatoms included in organic molecules include oxygen, nitrogen, sulfur and the like.

"Alcohol" refers, for example, to an alkyl moiety in which one or more of the hydrogen atoms has been replaced by an —OH group. The term "lower alcohol" refers, for example, to an alkyl group of about 1 to about 6 carbon atoms in which at least one, and optionally all, of the hydrogen atoms has been replaced by an —OH group.

"Amine" refers, for example, to an alkyl moiety in which one or more of the hydrogen atoms has been replaced by an —NH$_2$ group. The term "lower amine" refers, for example, to an alkyl group of about 1 to about 6 carbon atoms in which at least one, and optionally all, of the hydrogen atoms has been replaced by an —NH$_2$ group.

"Carbonyl compound" refers, for example, to an organic compound containing a carbonyl group, C=O, such as, for example, aldehydes, which have the general formula RCOH; ketones, which have the general formula RCOR'; carboxylic acids, which have the general formula RCOOH; and esters, which have the general formula RCOOR'.

The term "derivative" refers, for example, to compounds that are derived from another compound and maintain the same general structure as the compound from which they are derived. For example, saturated alcohols and saturated amines are derivatives of alkanes.

The term "homologous" refers, for example, to any number of series of organic compounds that have similar chemical properties and that differ by a constant relative molecular mass. For example, lower alcohols are a homologous series that includes CH$_3$OH, CH$_3$CH$_2$OH, CH$_3$CH$_2$CH$_2$OH, CH$_3$((CH$_2$)$_2$CH$_2$OH, CH$_3$(CH$_2$)$_3$CH$_2$OH and CH$_3$(CH$_2$)$_4$CH$_2$OH, as well as isomers of these molecules.

The term "saturated" refers, for example, to compounds containing only single bonds. The term "unsaturated" refers, for example, to compounds that contain one or more double bonds and/or one or more triple bonds.

The term "reflux" refers, for example, to the process of boiling a liquid, condensing the vapor and returning the vapor to the original container. When a liquid is refluxed, the temperature of the boiling liquid remains constant. The term "boiling point" refers, for example, to the temperature at which the saturated vapor pressure of a liquid is equal to the external atmospheric pressure.

The terms "standard temperature" and "standard pressure" refer, for example, to the standard conditions used as a basis where properties vary with temperature and/or pressure. Standard temperature is 0° C.; standard pressure is 101,325 Pa or 760.0 mmHg. The term "room temperature" refers, for example, to temperatures in a range of from about 20° C. to about 25° C.

The terms "high temperature environment" and "high temperature conditions" refer, for example, to an atmosphere in which the temperature is at least about 28 or about 30° C., and may be as high as about 300° C. The terms "high humidity environment" and "high humidity conditions" refer, for example, to an atmosphere in which the relative humidity is at least about 75 or about 80%.

The terms "one or more" and "at least one" herein mean that the description includes instances in which one of the subsequently described circumstances occurs, and that the description includes instances in which more than one of the subsequently described circumstances occurs.

An improved two-step process for producing triarylamines directly from a mono- or di-aryl amine (such as an aniline or a diaryl amine) and a halogenated aryl alcohol is provided. In a first step, a halogenated aryl (such as benzyl) alcohol such as 4-chlorobenzyl alcohol is protected to form a halogenated protected aryl alcohol compound such as a halogenated arylether compound (where the alcohol group is replaced with a methoxy or other group) by reacting the alcohol with an alcohol protecting agent (such as iodomethane and potassium hydroxide). In a second step, the halogenated protected aryl alcohol compound is reacted with a mono- or di-aryl amine (such as an aniline or a diaryl amine), such as in the presence of a suitable catalyst. For example, aniline can be rapidly reacted with 4-chlorobenzyl methyl ether to form, 4-(methoxymethyl)-N-(4-(methoxymethyl)phenyl)-N-phenyl aniline, or N,N-diphenyl amine can be rapidly reacted with 4-chlorobenzyl methyl ether to form, 4-(methoxymethyl)-N,N-diphenylaniline.

Figure 2:
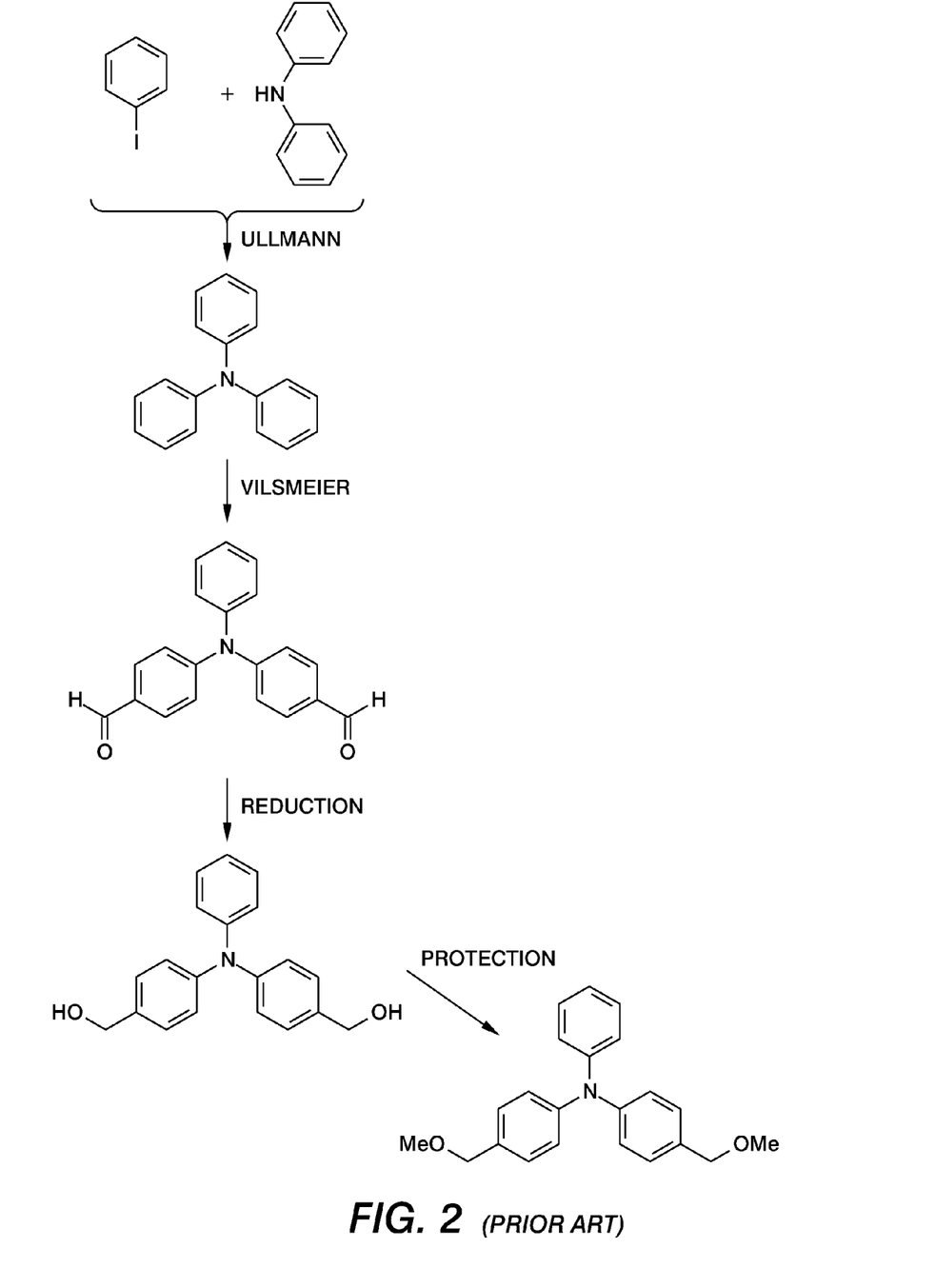
FIG. 2 represents a conventional process for producing a triarylamine.
Figure 3:
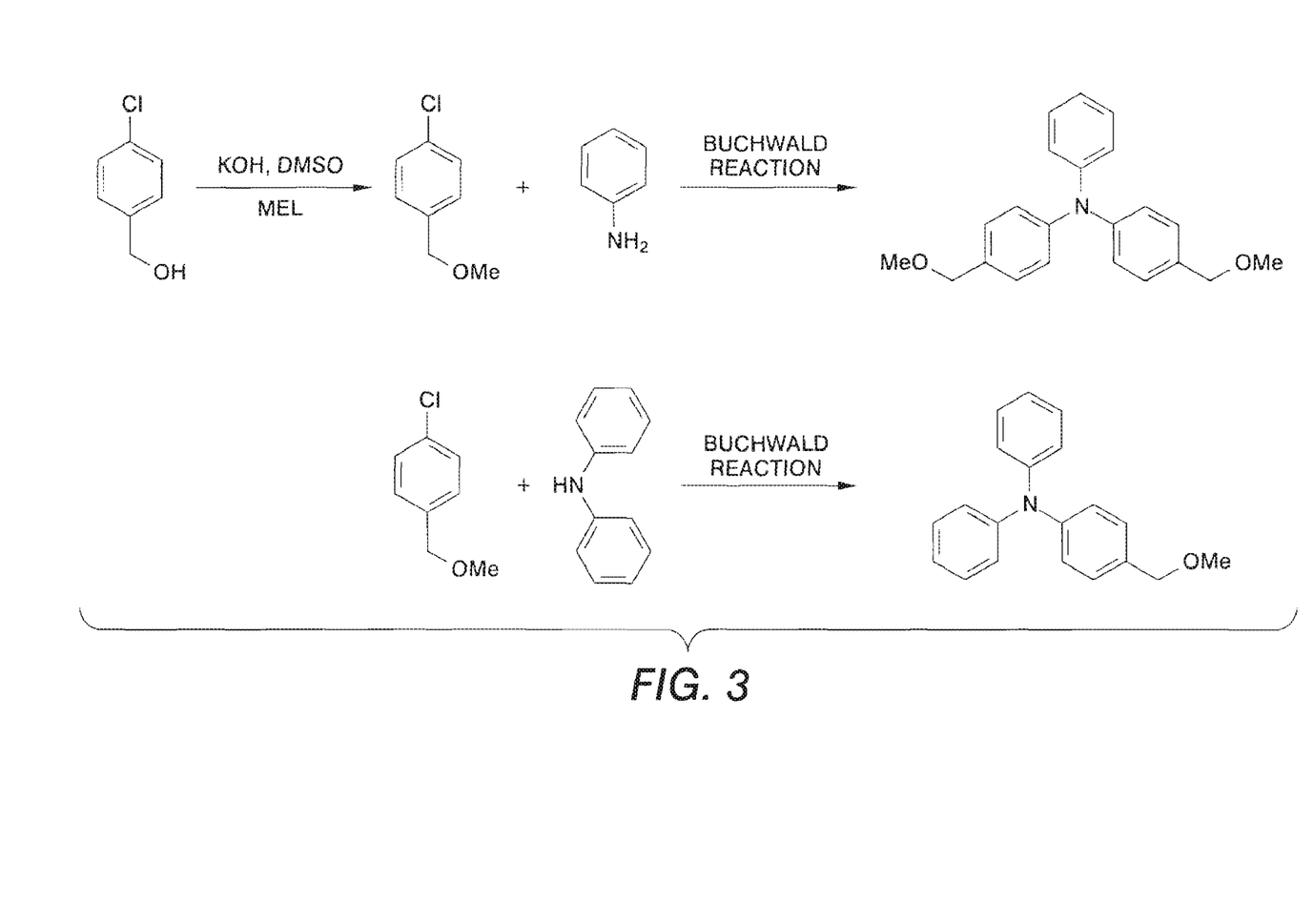
FIG. 3 represents processes for producing a triarylamine according to the disclosure.

The results surrounding this process were very unexpected in that the two-step process proceeding from the halogenated aryl alcohol and a mono- or di-aryl amine to the desired triarylamine proceeded easily and can be scaled-up to commercial scale, to produce triarylamine compounds. This process can be used in place of the longer four-step process that uses a Vilsmeier reaction. Furthermore, the process avoids not only the use of the non-commercially scaleable Vilsmeier reaction, but also avoids the use of corrosive Vilsmeier reagents such as POCl$_3$ or POBr$_3$ and the dangerous hydrogen reduction reactions. Therefore, this process is very practical and applicable to the preparation of triarylamines on an industrial scale since a two-step reaction produces a triarylamine in a short reaction time with high purity. This shorter, improved process is now described in detail. Compare, for example, FIG. 2, which shows a conventional four-step process for preparing a triarylamine, with FIG. 3, which shows the present two-step processes for preparing a triarylamine.

According to the processes of the present invention, a mono- or di-aryl amine and a halogenated aryl alcohol are used as starting materials. In general, the process of the present invention can be represented as:

where X is a halogen, such as chlorine, bromine, or iodine; n is 1 or 2; $R^1$ represents an alkyl group such as from 1 to about 50 carbon atoms or from 1 to about 20 carbon atoms or from 1 to about 10 carbon atoms; $R^2$ represents a suitable alcohol protecting group; and $Ar^1$ and $Ar^2$ independently represent aryl groups. The alcohol protecting group $R^2$ can be any suitable alcohol protecting group, such as an alkyl group, for example of from 1 to about 50 carbon atoms or from 1 to about 5 or to about 11 carbon atoms such as methyl, ethyl, propyl, isopropyl, butyl, isobutyl, tert-butyl, and the like, where the alkyl group can be straight or branched and substituted or unsubstituted, where the substitutions can include one or more groups selected from silyl groups, nitro groups, cyano groups, halide atoms, amine groups, hydroxy groups, alkoxy groups, aryloxy groups, alkylthio groups, arylthio groups, aldehyde groups, ketone groups, ester groups, amide groups, carboxylic acid groups, and sulfonic acid groups; a carbamate; a benzyl group; an acyl group, such as an acetyl group or a benzuyl group; a silyl group; an acid group; a sulfonate group; and the like. Any suitable alcohol protecting group can be used, so long as it can withstand the basic conditions of the subsequent Buchwald reaction. $Ar^1$ and $Ar^2$ can be any known substituted or unsubstituted aromatic component or a substituted or unsubstituted aryl group having from 2 to about 15 conjugate bonded or fused benzene rings and could include, but is not limited to, phenyl, naphthyl, anthryl, phenanthryl, and the like. The substituents on $Ar^1$ can be suitably selected to represent hydrogen, a halogen, an alkyl group having from 1 to about 20 carbon atoms, a hydrocarbon radical having from 1 to about 20 carbon atoms, an aryl group optionally substituted by one or more alkyl groups, an alkyl group containing a heteroatom such as oxygen, nitrogen, sulfur, and the like, having from 1 to about 20 carbon atoms, a hydrocarbon radical containing a heteroatom such as oxygen, nitrogen, sulfur, and the like, having from 1 to about 20 carbon atoms, an aryl group containing a heteroatom such as oxygen, nitrogen, sulfur, and the like, optionally substituted by one or more alkyl groups, and the like.

In particular embodiments, the processes of the present invention, including the starting materials and final product, can generally be represented as follows:

In this reaction scheme, the mono- or di-aryl amine and the halogenated aryl alcohol can be any suitable compound, depending on the desired final product. Thus, for example, in the above reaction scheme, each of $Ar^1$ and $Ar^2$ can be any known substituted or unsubstituted aromatic component or a substituted or unsubstituted aryl group having from 2 to about 15 conjugate bonded or fused benzene rings and could include, but is not limited to, phenyl, naphthyl, anthryl, phenanthryl, and the like. The substituents on $Ar^1$ and $Ar^2$ can be suitably selected to represent hydrogen, a halogen, an alkyl group having from 1 to about 20 carbon atoms, a, hydrocarbon radical having from 1 to about 20 carbon atoms, an aryl group optionally substituted by one or more alkyl groups, an alkyl group containing a heteroatom such as oxygen, nitrogen, sulfur, and the like, having from 1 to about 20 carbon atoms, a hydrocarbon radical containing a heteroatom such as oxygen, nitrogen, sulfur, and the like, having from 1 to about 20 carbon atoms, an aryl group containing a heteroatom such as oxygen, nitrogen, sulfur, and the like, optionally substituted by one or more alkyl groups, and the like. Depending upon the desired final product, a monoarylamine (n=1) or a diarylamine (n=2) can be selected.

In the first step of the two-step process, the halogenated aryl alcohol is converted to a halogenated protected aryl alcohol compound to protect the alcohol group. This reaction step generally comprises reacting the halogenated aryl alcohol with an alcohol protecting agent and a base. Any suitable alcohol protecting agents can be used, and selection will depend upon the desired final product. For example, where the alcohol group is to be protected using a methyl group, a suitable alcohol protecting agent is iodomethane. Other suitable methylating reagents that can be used as the alcohol protecting agent include methyl chloride, methyl bromide, dimethyl sulfate, dimethyl carbonate, and the like. Likewise, other suitable alcohol protecting agents can be used, and are known in the art.

Any suitable base may be used in embodiments, such as an alkaline hydroxide or an alkaline alkoxide and the like. Exemplary bases that may be used in embodiments include bases having the general formula MOR, in which O is oxygen, M is a metal atom, and R is a hydrogen or an alkyl group. M is a metal selected from potassium, sodium, lithium, calcium, magnesium and the like; and R is a hydrogen or a straight or branched alkyl group selected from methyl, ethyl, propyl, butyl, pentyl, hexyl, heptyl, octyl, nonyl, and decyl groups, such as methyl, ethyl, n-propyl, isopropyl, n-butyl, isobutyl, tert-butyl, octyl, decyl and the like. Suitable bases include potassium hydroxide, potassium tert-butoxide salt, sodium tert-butoxide, and sodium tert-pentoxide.

The reaction can be conducted in any suitable medium, such as a suitable solvent medium, as necessary or desired. In embodiments, the solvent used for the first step is desirably a polar aprotic solvent. For example, a suitable solvent for conducting the reaction is dimethylsulfoxide. Other suitable solvents include dimethylformamide, dimethylacetamide dioxane, tetrahydrofuran, acetone, methyl ethyl ketone, acetonitrile, and the like.

In the second step of the two-step process, the halogenated protected aryl alcohol compound is reacted with an amine, such as the mono- or di-aryl amine, to produce the desired triarylamine compound. This reaction step generally comprises reacting the halogenated protected aryl alcohol compound with the mono- or di-aryl amine under suitable reaction conditions. For example, one suitable reaction scheme is to react the materials under Buchwald reaction conditions, that is, with a base and in the presence of a suitable catalyst. The base can be any suitable base, including those bases described above for use in the first step of the process. The catalyst is also not particularly limited, and suitable catalysts include those that are known or discovered to be useful for formation of nitrogen-carbon bonds. For example, suitable catalysts include ligated palladium catalysts, such as those disclosed by Buchwald et al. and Hartwig et al. (see, e.g., *J. Org. Chem.* 2000, 65, 5327-5333, the entire disclosure of which is incorporated herein by reference).

In an embodiment of the present disclosure, an example of a suitable catalyst is palladium acetate ligated with tri-t-butylphosphine in the presence of a base. In another embodiment of the present disclosure, an example of a suitable catalyst is palladium acetate ligated with a phospha-adamantane molecule given by structural formula (I):

in the presence of a base, where each X individually represents either $CH_2$ or an oxygen atom; $Y^1$, $Y^2$, $Y^3$, and $Y^4$ each individually represent a substituted or unsubstituted, straight or branched, alkyl, alkenyl, or alkynyl group having from 1 to about 10 carbon atoms, such as from 1 to about 5, or from 1 to about 3 carbon atoms; and $Y^5$ represents hydrogen, a substituted or unsubstituted alkyl group, or an aryl group. One specific molecule given by formula (I) is 2,4,6-trioxa-1,3,5,7-tetramethyl-8-phosphaadamantane, which is manufactured as Cytop-216 (Cytec Industries). However, it will be apparent to those skilled in the art that other ligands, such as any tertiary phosphine ligand such as biaryldialkylphosphine or trialkyl phosphine ligands, or N-heterocyclic carbene complexes could also be used to produce suitable results (from the point of view of conversion and yield), and thus would be suitable to ligate palladium or other metals and thus act as catalysts for the process described in this disclosure.

Another suitable reaction scheme is to react the materials under Ullmann reaction conditions, that is, in the presence of a suitable catalyst and a base, optionally in the presence of a high boiling hydrocarbon such as decane as a solvent. Examples of the suitable base that can be used in the process include alkali metal hydroxides such as lithium hydroxide, sodium hydroxide, potassium hydroxide, rubidium hydroxide, and cesium hydroxide; alkali metal carbonates such as lithium carbonate, sodium carbonate, potassium carbonate, rubidium carbonate, and cesium carbonate; alkali metal phosphates such as trilithium phosphate, trisodium phosphate, and tripotassium phosphate; and alkali metal alkoxides such as sodium methoxide, sodium ethoxide, potassium methoxide, potassium ethoxide, lithium tert-butoxide, sodium tert-butoxide, and potassium tert-butoxide. Of these bases, the alkali metal alkoxides may be added as they are to the reaction system or may be prepared from the alkali metals, alkali metal hydrides, alkali metal hydroxides, or the like and an alcohol and used. Specific examples of suitable bases are sodium hydroxide, potassium hydroxide, sodium carbonate, and potassium carbonate. These bases can generally be used in an amount of about 1 to about 4 equivalents, such as about 1.2 to about 2.0 equivalents, to the aromatic amine. Examples of suitable catalysts include copper catalysts, such as copper powder, copper (I) chloride, copper (II) chloride, copper (I) bromide, copper (II) bromide, copper iodide, copper (I) oxide, copper (II) oxide, copper sulfate, copper nitrate, copper carbonate, and copper (II) hydroxide. Specific suitable examples include copper (I) oxide, copper chlorides, copper bromides, and copper iodide. The amount of these copper catalysts to be used is generally about 0.001 to about 0.3 mol, such as about 0.01 to about 0.2 mol, per mol of the aromatic halogen compound. If desired or necessary, a promoter such as lithium iodide, sodium iodide, potassium iodide, rubidium iodide, cesium iodide, or the like may be added. In the case where these promoters are added, they can be used in an amount of about 0.001 to about 0.5 mol, such as about 0.01 to about 0.2 mol, per mol of the aromatic halogen compound.

As a modification of the Ullmann reaction, a ligand-accelerated Ullmann reaction can also be used. This reaction is generally also conducted in the presence of a catalyst, such as the catalysts described above for the standard Ullmann reaction, but also in the presence of a bidentate ligand of the following formulas:

wherein 0 or 1 of the carbon atoms are replaced with N, or wherein from 0 to 3 of the carbon atoms are replaced with N, or the compound is benzo-fused and 0 to 2 of the carbon atoms of the five-membered ring are replaced with N; and wherein:
$X^1$ is selected from Cl, Br, I, and SCN;
$X^2$ is selected from Br or I;
$R^1$ is selected from H, Cl, F, Br, I, $C_{1-4}$ alkyl, $C_{1-4}$ alkoxy, $C_{1-4}$ alkylene-O—$C_{1-4}$ alkyl, $NH_2$, $NH(C_{1-4}$ alkyl), $N(C_{1-4}$ alkyl)$_2$, $C_{1-4}$ alkylene-$NH_2$, $C_{1-4}$ alkylene-$NH(C_{1-4}$ alkyl), $C_{1-4}$ alkylene-$N(C_{1-4}$ alkyl)$_2$, $C_{3-10}$ carbocycle substituted with 0-2 $R^3$, 5-6 membered heterocycle comprising carbon atoms and 1-4 heteroatoms selected from N, O, and S and substituted with 0-2 $R^3$;
$R^2$ is selected from H, Cl, F, Br, I, $C_{1-4}$ alkyl, $C_{1-4}$ alkoxy, $C_{1-4}$ alkylene-O—$C_{1-4}$ alkyl, $NH_2$, $NH(C_{1-4}$ alkyl), $N(C_{1-4}$ alkyl)$_2$, $C_{1-4}$ alkylene-$NH_2$, $C_{1-4}$ alkylene-$NH(C_{1-4}$ alkyl), $C_{1-4}$ alkylene-$N(C_{1-4}$ alkyl)$_2$, $C_{3-10}$ carbocycle substituted with 0-2 $R^3$, 5-6 membered heterocycle comprising carbon atoms and 1-4 heteroatoms selected from N, O, and S and substituted with 0-2 $R^3$;
$R^3$ is selected from Cl, F, Br, I, $C_{1-4}$ alkyl, $C_{1-4}$ alkoxy, $C_{1-4}$ alkylene-O—$C_{1-4}$ alkyl, $NH_2$, $NH(C_{1-4}$ alkyl), $N(C_{1-4}$ alkyl)$_2$, $C_{1-4}$ alkylene-$NH_2$, $C_{1-4}$ alkylene-$NH(C_{1-4}$ alkyl), $C_{1-4}$ alkylene-$N(C_{1-4}$ alkyl)$_2$, and $NO_2$;
r is 1 or 2; and,
the bidentate ligand is a hydrolytically stabile ligand that ligates with Cu(I) and comprises two heteroatoms selected from N and O.

In embodiments, suitable specific examples of the bidentate ligand include tetramethylethylenediamine (TMED), 2,2'-dipyridyl (DPD), 8-hydroxyquinoline (HQL), 1,10-phenanthroline (PNT), 8-hydroxyquinoline (HQL), and 1,10-phenanthroline (PNT). The bidentate ligand can be used in any desired and suitable amount, such as from about 0.001 to about 0.5 equivalents, based on the molar amount of aniline present.

The reaction of the second step of the process can be carried out in the presence of the catalyst, and can be conducted in continuous mode. However, the reaction may be conducted in batch mode. For example, the reaction can be carried out for a period of from about 2 to about 30 hours or more, such as a reaction time of from about 4 to about 6 hours.

The reaction of the second step of the process can be carried out in a suitable solvent, such as toluene, xylene, decane, other hydrocarbon solvents (either aromatic or saturated hydrocarbons), or mixtures thereof. The choice of solvent can be decided based on the solubility of the starting materials, intermediates, and final products, and will be readily apparent or within routine experimentation to those skilled in the art. Furthermore the choice of solvent can be decided based on the desired operating temperature range. The described process is exothermic and precautions should be taken to ensure that the solvent chosen is capable of dispersing the produced heat by, for example, refluxing and cooling at such a rate so as to control the exotherm. The reaction should be conducted under an atmosphere of inert gas (such as nitrogen or argon) so as to preclude deactivation of catalyst or base by oxygen or atmospheric moisture.

In embodiments, as desired, the solvents used in the first and second steps can be the same or different. Likewise, the bases used in the first and second steps can be the same or different.

After the reaction is completed, suitable separation, filtration, and/or purification processes can be conducted, as desired to a desired purity level. For example, the desired triarylamine product can be subjected to conventional organic washing steps, can be separated, can be decolorized (if necessary, treated with known absorbents (such as silica, alumina, and clays, if necessary) and the like. The final product can be isolated, for example, by a suitable recrystallization procedure. The final product can also be dried, for example, by air drying, vacuum drying, or the like. All of these procedures are conventional and will be apparent to those skilled in the art.

The triarylamine produced by this process can be further processed and/or reacted to provide other compounds for their separate use. For example, the triarylamine can be further processed and/or reacted to provide charge-transport materials or other compounds useful in such electrostatographic imaging member. An exemplary electrostatographic imaging member will now be described in greater detail.

Figure 1:
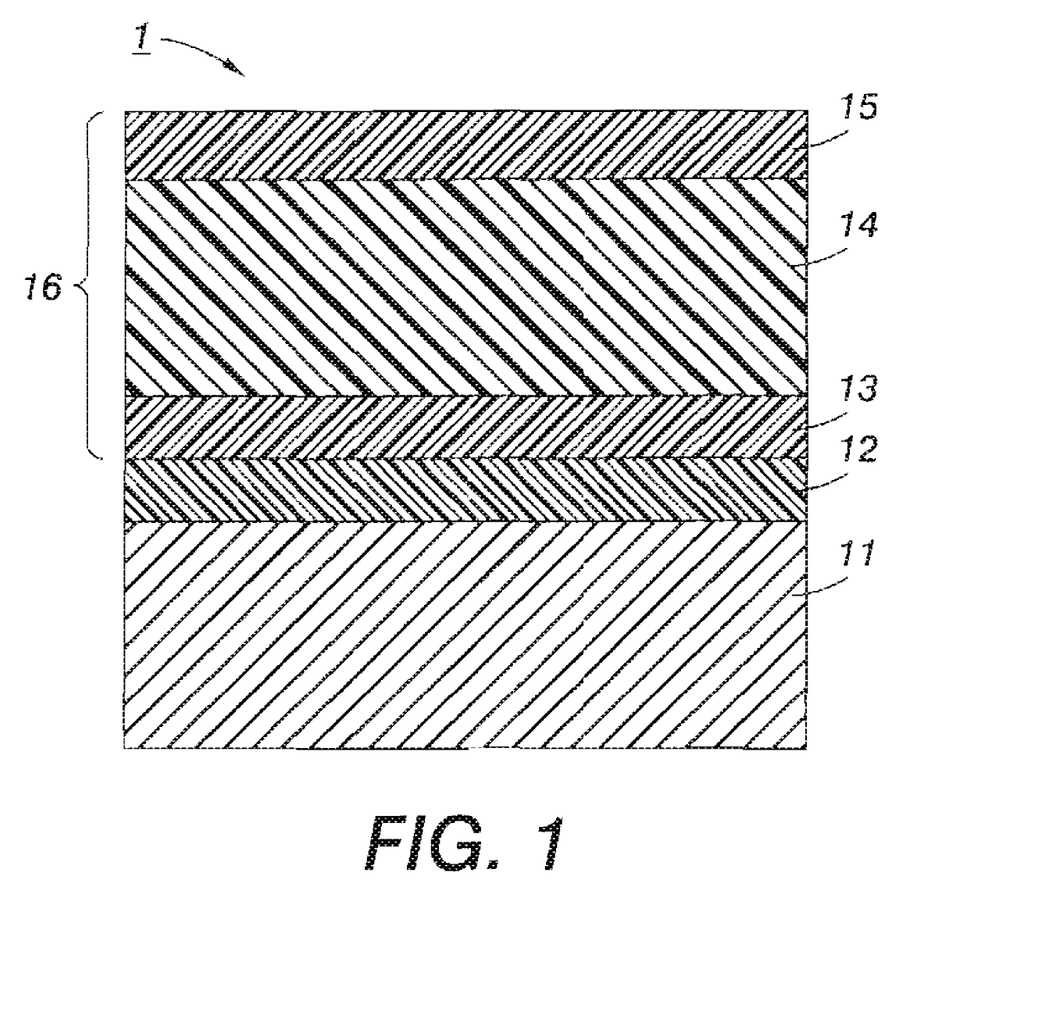
FIG. 1 is a schematic cross sectional view showing an embodiment of an electrophotographic photoreceptor of the disclosure.

The FIGURE is a cross-sectional view schematically showing an embodiment of the electrophotographic photoreceptor of the disclosure. The electrophotographic photoreceptor 1 shown in the FIGURE is a function-separation-type photoreceptor in which a charge-generation layer 13 and a charge-transport layer 14 are separately provided. That is, an underlayer 12, the charge-generation layer 13, the charge transport layer 14 and a protective layer 15 are laminated onto a conductive support 11 to form a photosensitive layer 16. The protective layer 15 contains a resin soluble in the liquid component contained in the coating solution used for formation of this layer and the silicon compound. The various layers of the photoreceptor are generally known, and are described in detail in the above-mentioned commonly owned and co-pending applications.

The photoconductive members are, in embodiments, multilayered photoreceptors that comprise a substrate, an optional conductive layer, an optional undercoat layer, an optional adhesive layer, a charge generating layer, a charge transport layer, and an overcoat layer.

Illustrative examples of substrate layers selected for the photoconductive imaging members, and which substrates may be known substrates and which can be opaque or substantially transparent, comprise a layer of insulating material including inorganic or organic polymeric materials, such as MYLAR®, a commercially available polymer, MYLAR® containing titanium, a layer of an organic or inorganic material having a semiconductive surface layer, such as indium tin oxide, or aluminum arranged thereon, or a conductive material inclusive of aluminum, chromium, nickel, brass or the like. The substrate may be flexible, seamless, or rigid, and may have a number of many different configurations, such as, a plate, a cylindrical drum, a scroll, an endless flexible belt, and the like. In one embodiment, the substrate is in the form of a seamless flexible belt. In some situations, it may be desirable to coat on the back of the substrate, particularly when the substrate is a flexible organic polymeric material, an anticurl layer, such as polycarbonate materials commercially available as MAKROLON®.

The thickness of the substrate layer depends on a number of factors, including the characteristics desired and economical considerations, thus this layer may be of substantial thickness, such as over 3,000 microns, such as from about 3,000 to about 7,000 microns or of minimum thickness, such as at least about 50 microns, providing there are no significant adverse effects on the member. In embodiments, the thickness of this layer is from about 75 microns to about 300 microns.

If a conductive layer is used, it is positioned over the substrate. The term "over" as used herein in connection with many different types of layers, as well as the term "under," should be understood as not being limited to instances where the specified layers are contiguous. Rather, the term refers to relative placement of the layers and encompasses the inclusion of unspecified intermediate layers between the specified layers.

Suitable materials for the conductive layer include aluminum, zirconium, niobium, tantalum, vanadium, hafnium, titanium, nickel, stainless steel, chromium, tungsten, molybdenum, copper, and the like, and mixtures and alloys thereof.

The thickness of the conductive layer is, in one embodiment, from about 20 angstroms to about 750 angstroms, and, in another from about 50 angstroms to about 200 angstroms, for a suitable combination of electrical conductivity, flexibility, and light transmission. However, the conductive layer can, if desired, be opaque.

The conductive layer can be applied by known coating techniques, such as solution coating, vapor deposition, and sputtering. In embodiments, an electrically conductive layer is applied by vacuum deposition. Other suitable methods can also be used.

If an undercoat layer is employed, it may be positioned over the substrate, but under the charge generating layer. The undercoat layer is at times referred to as a hole-blocking layer in the art.

Suitable undercoat layers for use herein include polymers, such as polyvinyl butyral, epoxy resins, polyesters, polysiloxanes, polyamides, polyurethanes, and the like, nitrogen-containing siloxanes or nitrogen-containing titanium compounds, such as trimethoxysilyl propyl ethylene diamine, N-beta (aminoethyl) gamma-aminopropyl trimethoxy silane, isopropyl 4-aminobenzene sulfonyl titanate, di(dodecylbenezene sulfonyl) titanate, isopropyl di(4-aminobenzoyl) isostearoyl titanate, isopropyl tri(N-ethyl amino) titanate, isopropyl trianthranil titanate, isopropyl tri(N,N-(dimethyl-ethyl amino) titanate, titanium-4-amino benzene sulfonate oxyacetate, titanium 4-aminobenzoate isostearate oxyacetate, gamma-aminobutyl methyl dimethoxy silane, gamma-aminopropyl methyl dimethoxy silane, and gamma-aminopropyl trimethoxy silane, as disclosed in U.S. Pat. Nos. 4,338,387, 4,286,033 and 4,291,110.

The undercoat layer may be applied as a coating by any suitable conventional technique such as spraying, die coating, dip coating, draw bar coating, gravure coating, silk screening, air knife coating, reverse roll coating, vacuum deposition, chemical treatment and the like. For convenience in obtaining layers, the undercoat layers may be applied in the form of a dilute solution, with the solvent being removed after deposition of the coating by conventional techniques such as by vacuum, heating and the like. Drying of the deposited coating may be achieved by any suitable technique such as oven drying, infrared radiation drying, air drying and the like.

In fabricating a photoconductive imaging member, a charge generating layer is deposited and a charge transport layer may be deposited onto the substrate surface either in a laminate type configuration where the charge generating layer and charge transport layer are in different layers or in a single layer configuration where the charge generating layer and charge transport layer are in the same layer along with a binder resin. In embodiments, the charge generating layer is applied prior to the charge transport layer.

The charge generating layer is positioned over the undercoat layer. If an undercoat layer is not used, the charge generating layer is positioned over the substrate. In embodiments, the charge generating layer is comprised of amorphous films of selenium and alloys of selenium and arsenic, tellurium, germanium and the like, hydrogenated amorphous silicon and compounds of silicon and germanium, carbon, oxygen, nitrogen and the like fabricated by vacuum evaporation or deposition. The charge generating layers may also comprise inorganic pigments of crystalline selenium and its alloys; (Group II-VI compounds; and organic pigments such as quinacridones, polycyclic pigments such as dibromo anthanthrone pigments, perylene and perinone diamines, polynuclear aromatic quinones, azo pigments including bis-, tris- and tetrakis-azos; and the like dispersed in a film forming polymeric binder and fabricated by solvent coating techniques.

Phthalocyanines have been employed as photogenerating materials for use in laser printers using infrared exposure systems. Infrared sensitivity is desired for photoreceptors exposed to low-cost semiconductor laser diode light exposure devices. The absorption spectrum and photosensitivity of the phthalocyanines depend on the central metal atom of the compound. Many metal phthalocyanines have been reported and include, oxyvanadium phthalocyanine, chloroaluminum phthalocyanine, copper phthalocyanine, oxytitanium phthalocyanine, chlorogallium phthalocyanine, hydroxygallium phthalocyanine magnesium phthalocyanine and metal-free phthalocyanine. The phthalocyanines exist in many crystal forms, and have a strong influence on photogeneration.

Any suitable polymeric film-forming binder material may be employed as the matrix in the charge generating (photogenerating) binder layer. Typical polymeric film forming materials include those described, such as, in U.S. Pat. No. 3,121,006, the entire disclosure of which is incorporated herein by reference. Thus, typical organic polymeric film forming binders include thermoplastic and thermosetting resins such as polycarbonates, polyesters, polyamides, polyurethanes, polystyrenes, polyarylethers, polyarylsulfones, polybutadienes, polysulfones, polyethersulfones, polyethylenes, polypropylenes, polyimides, polymethylpentenes, polyphenylene sulfides, polyvinyl acetate, polysiloxanes, polyacrylates, polyvinyl acetals, polyamides, polyimides, amino resins, phenylene oxide resins, terephthalic acid resins, phenoxy resins, epoxy resins, phenolic resins, polystyrene and acrylonitrile copolymers, polyvinylchloride, vinylchloride and vinyl acetate copolymers, acrylate copolymers, alkyd resins, cellulosic film formers, poly(amideimide), styrene-butadiene copolymers, vinylidenechloride-vinylchloride copolymers, vinylacetate-vinylidenechloride copolymers, styrene-alkyd resins, polyvinylcarbazole, and the like. These polymers may be block, random or alternating copolymers.

A photogenerating composition or pigment may be present in the resinous binder composition in various amounts. Generally, however, from about 5 percent by volume to about 90 percent by volume of the photogenerating pigment is dispersed in about 10 percent by volume to about 95 percent by volume of the resinous binder, and typically from about 20 percent by volume to about 30 percent by volume of the photogenerating pigment is dispersed in about 70 percent by volume to about 80 percent by volume of the resinous binder composition. The photogenerator layers can also fabricated by vacuum sublimation in which case there is no binder.

In embodiments, any suitable technique may be used to mix and thereafter apply the photogenerating layer coating mixture. Typical application techniques include spraying, dip coating, roll coating, wire wound rod coating, vacuum sublimation and the like. For some applications, the charge generating layer may be fabricated in a dot or line pattern. Removing of the solvent of a solvent coated layer may be effected by any suitable technique such as oven drying, infrared radiation drying, air drying and the like. In embodiments, the charge generating layer is from about 0.1 micrometers to about 100 micrometers thick, such as from about 0.1 micrometers to about 50 micrometers.

In embodiments, a charge transport layer may be employed. The charge transport layer may comprise a charge-transporting molecule, such as, a small molecule, dissolved or molecularly dispersed in a film forming electrically inert polymer such as a polycarbonate. The expression charge transporting "small molecule" is defined herein as a monomer that allows the free charge photogenerated in the generator layer to be transported across the transport layer. In embodiments, the term "dissolved" refers to, for example, forming a solution in which the molecules are distributed in the polymer to form a homogeneous phase. In embodiments, the expression "molecularly dispersed" refers to a dispersion in which a charge transporting small molecule dispersed in the polymer, for example on a molecular scale.

Any suitable charge transporting or electrically active small molecule may be employed in the charge transport layer.

Typical charge transporting molecules include, for example, pyrene, carbazole, hydrazone, oxazole, oxadiazole, pyrazoline, arylamine, arylmethane, benzidine, thiazole, stilbene and butadiene compounds; pyrazolines such as 1-phenyl-3-(4'-diethylaminostyryl)-5-(4'-diethylamino phenyl) pyrazoline; diamines such as N,N'-diphenyl-N,N'-bis(3-methylphenyl)-(1,1'-biphenyl)-4,4'-diamine; hydrazones such as N-phenyl-N-methyl-3-(9-ethyl)carbazyl hydrazone and 4-diethyl amino benzaldehyde-1,2-diphenyl hydrazone; oxadiazoles such as 2,5-bis (4-N,N'-diethylaminophenyl)-1, 2,4-oxadiazole; poly-N-vinylcarbazole, poly-N-vinylcarbazole halide, polyvinyl pyrene, polyvinylanthracene, polyvinylacridine, a pyrene-formaldehyde resin, an ethylcarbazole-formaldehyde resin, a triphenylmethane polymer and polysilane, and the like.

In embodiments, to minimize or avoid cycle-up in machines with high throughput, the charge transport layer may be substantially free (such as, from zero to less than about two percent by weight of the charge transport layer) of triphenylmethane. As indicated above, suitable electrically active small molecule charge transporting compounds are dissolved or molecularly dispersed in electrically inactive polymeric film forming materials.

An exemplary small molecule charge transporting compound that permits injection of holes from the pigment into the charge generating layer with high efficiency and transports them across the charge transport layer with very short transit times is N,N'-diphenyl-N,N'-bis(3-methylphenyl)-(1, 1'-biphenyl)-4,4'-diamine. If desired, the charge transport material in the charge transport layer may comprise a polymeric charge transport material or a combination of a small molecule charge transport material and a polymeric charge transport material.

In embodiments, the charge transport layer may contain an active aromatic diamine molecule, which enables charge transport, dissolved or molecularly dispersed in a film forming binder. An exemplary, charge transport layer is disclosed in U.S. Pat. No. 4,265,990, the entire disclosure of which is incorporated herein by reference.

Any suitable electrically inactive resin binder that is ideally substantially insoluble in the solvent such as alcoholic solvent used to apply the optional overcoat layer may be employed in the charge transport layer. Typical inactive resin binders include polycarbonate resin, polyester, polyarylate, polyacrylate, polyether, polysulfone, and the like. Molecular weights can vary, such as from about 20,000 to about 150,000. Exemplary binders include polycarbonates such as poly (4,4'-isopropylidene-diphenylene)carbonate (also referred to as bisphenol-A-polycarbonate); polycarbonate, poly (4,4'-cyclohexylidinediphenylene) carbonate (referred to as bisphenol-Z polycarbonate), poly (4,4'-isopropylidene-3,3'-dimethyl-diphenyl)carbonate (also referred to as bisphenol-C-polycarbonate), and the like.

Any suitable charge transporting polymer may also be utilized in the charge transporting layer of this disclosure. The charge transporting polymer should be insoluble in the solvent employed to apply the overcoat layer. These electrically active charge transporting polymeric materials should be capable of supporting the injection of photogenerated holes from the charge generating material and be capable of allowing the transport of these holes therethrough.

Any suitable technique may be utilized to mix and thereafter apply the charge transport layer coating mixture to the charge generating layer. Typical application techniques include spraying, dip coating, roll coating, wire wound rod coating, and the like. Drying of the deposited coating may be effected by any suitable technique such as oven drying, infrared radiation drying, air drying and the like.

Generally, the thickness of the charge transport layer is from about 10 to about 100 micrometers, but a thickness outside this range can also be used. A charge transport layer should be an insulator to the extent that the electrostatic charge placed on the charge transport layer is not conducted in the absence of illumination at a rate sufficient to prevent formation and retention of an electrostatic latent image thereon. In general, the ratio of the thickness of a charge transport layer to the charge generating layers may be maintained from about 2:1 to 200:1, and in some instances as great as 400:1. Typically, a charge transport layer is substantially non-absorbing to visible light or radiation in the region of intended use but is electrically "active" in that it allows the injection of photogenerated holes from the photoconductive layer, i.e., charge generation layer, and allows these holes to be transported through itself to selectively discharge a surface charge on the surface of the active layer.

Additionally, adhesive layers can be provided, if necessary or desired, between any of the layers in the photoreceptors to ensure adhesion of any adjacent layers. Alternatively, or in addition, adhesive material can be incorporated into one or both of the respective layers to be adhered. Such optional adhesive layers may have a thickness of about 0.001 micrometer to about 0.2 micrometer. Such an adhesive layer can be applied, for example, by dissolving adhesive material in an appropriate solvent, applying by hand, spraying, dip coating, draw bar coating, gravure coating, silk screening, air knife coating, vacuum deposition, chemical treatment, roll coating, wire wound rod coating, and the like, and drying to remove the solvent. Suitable adhesives include film-forming polymers, such as polyester, DuPont 49,000 (available from E. I. DuPont de Nemours & Co.), VITEL PE-100 (available from Goodyear Tire and Rubber Co.), polyvinyl butyral, polyvinyl pyrrolidone, polyurethane, polymethyl methacrylate, and the like.

Optionally, an anti-curl backing layer may be employed to balance the total forces of the layer or layers on the opposite side of the supporting substrate layer. An example of an anti-curl backing layer is described in U.S. Pat. No. 4,654,284, the entire disclosure of which is incorporated herein by reference. A thickness from about 70 to about 160 micrometers may be a satisfactory range for flexible photoreceptors.

The overcoat layer generally comprises the cured or substantially crosslinked product of at least a phenolic resin and/or phenol compound and a charge transport compound. The phenolic overcoat layer may further comprise a polymer binder. "Cured" herein refers to, for example, a state in which the phenolic resin and/or phenol compounds in the overcoat coating solution have reacted with each other and/or the charge transport compound to form a substantially crosslinked product. Substantially crosslinked in embodiments refers to, for example, a state in which about 60% to 100% of the reactive components of the overcoat coating composition, for example about 70% to 100% or about 80% to 100%.

The curing or crosslinking of the reactive components occurs, in embodiments, following application of the overcoat coating composition to the previously formed structure of the imaging member. The overcoat coating composition thus comprises at least the phenolic resin and/or phenol compound(s) and the charge transport compound.

In embodiments, the overcoat layer comprises the cured or substantially crosslinked product of at least a phenol compound and a charge transport compound. The term "phenol compound" may include phenolic resins as disclosed herein.

The electrophotographic photoreceptor of embodiments may be either a function-separation-type photoreceptor, in which a layer containing a charge-generation substance (charge-generation layer) and a layer containing a charge-transport substance (charge-transport layer) are separately provided, or a monolayer-type photoreceptor, in which both the charge-generation layer and the charge-transport layer are contained in the same layer.

Specific examples are described in detail below. These examples are intended to be illustrative, and the materials, conditions, and process parameters set forth in these exemplary embodiments are not limiting. All parts and percentages are by weight unless otherwise indicated.

EXAMPLES

The invention will be illustrated in greater detail with reference to the following Example, but the invention should not be construed as being limited thereto. In the following example, all the "parts" are given by weight unless otherwise indicated.

Example 1

Protection of 4-chlorobenzyl Alcohol:

Dimethyl sulfoxide (300 mL) was placed into a 1 L round bottom flask under argon. The KOH (78.7 g, 1402 mmol) was then added and this was stirred for 15 minutes until most of the KOH dissolved. The 4-chlorobenzyl alcohol (50 g, 350.65 mmol) and then iodomethane (99.5 g, 701.3 mmol) were then added. The reaction was stirred at room temperature under argon overnight. Cyclohexane (300 mL) was then added and this was stirred for 1 hour. The layers were separated and the cyclohexane was washed twice with 50% brine solution. The organic layer was collected, dried ($MgSO_4$) and concentrated in vacuo to give a yellowish oil, which was purified by distillation to give a clear and colorless oil in 82% yield.

Buchwald Reaction:

To a 500 mL 3-necked round bottom flask equipped with a mechanical stirrer, argon inlet, thermometer and reflux condenser was placed (1,3-diisopropylimidazol-2-ylidene)(3-chloropyridyl) palladium(II) dichloride (2.19 g, 3.2 mmol) and was dissolved in toluene (50 mL) under argon. Then aniline (10 g, 107.4 mmol), the protected 4-chlorobenzyl alcohol (50.30 g, 322.2 mmol) and then sodium tert-butoxide (20.6 g, 214.8 mmol) were added. The reaction was stirred under argon at 110° C. until the reaction was complete, usually 3 hours. The reaction was then cooled and then washed twice with a 50% aqueous brine solution. The organic layer was collected, dried ($MgSO_4$) and then treated with 20 g each of an acidified clay and alumina at 100° C. for 30 minutes. The solids were filtered and the filtrate was concentrated under reduced pressure to produce a light yellow oil in 75% yield. NMR confirmed that the desired triarylamine, 4-(methoxymethyl)-N-(4-(methoxymethyl)phenyl)-N-phenylaniline was obtained.

Example 2

To a 500 mL 3-necked round bottom flask equipped with a mechanical stirrer, argon inlet, thermometer and reflux condenser was placed palladium acetate (0.398 g, 1.773 mmol), cytop-216 (0.493 g, 1.773 mmol) and was dissolved in xylene (150 mL) under argon. Then diphenylamine (10 g, 59.1 mmol), the protected 4-bromobenzyl alcohol (14.26 g, 70.9 mmol) and then sodium tert-butoxide (8.52 g, 89 mmol) were added. The reaction was stirred under argon at 130° C. until the reaction was complete. The reaction was then cooled and then washed twice with a 50% aqueous brine solution. The organic layer was collected, dried (MgSO$_4$) and then treated with 30 g each of an acidified clay and alumina at 100° C. for 30 minutes. The solids were filtered and the filtrate was concentrated under reduced pressure to produce an off white solid in good yield. NMR would confirm that the desired triarylamine 4-(methoxymethyl)-N,N-diphenylaniline was obtained.

While this procedure represents an example conducted at laboratory scale, the process is readily scaleable to commercial scale.

It will be appreciated that various of the above-discussed and other features and functions, or alternatives thereof, may be desirably combined into many other different systems or applications. Also that various presently unforeseen or unanticipated alternatives, modifications or improvements therein may be subsequently made by those skilled in the art which are also intended to be encompassed by the following claims.

What is claimed is:

1. A process for forming a triarylamine compound, comprising:
   (1) reacting a halogenated aryl alcohol with an alcohol protecting agent and a first base to form a halogenated protected aryl alcohol compound, and
   (2) reacting the halogenated protected aryl alcohol compound with an amine in the presence of a suitable palladium catalyst and a second base.

2. The process of claim 1, wherein the halogenated aryl alcohol, halogenated arylether compound, and amine are represented as follows:

wherein:
X is a halogen,
n is 1 or 2,
R$^1$ represents an alkyl group of from 1 to about 50 carbon atoms,
R$^2$ represents a suitable alcohol protecting group, and
Ar$^1$ and Ar$^2$, which can be the same or different, are selected from the group consisting of substituted or unsubstituted aromatic components, and substituted or unsubstituted aryl groups having from 2 to about 15 conjugate bonded or fused benzene rings, wherein a substituent on the aryl groups Ar1 and Ar2 is selected from the group consisting of hydrogen, a halogen, an alkyl group having from 1 to about 20 carbon atoms, a hydrocarbon radical having from 1 to about 20 carbon atoms, an aryl group, an aryl group substituted by one or more alkyl groups, an alkyl group containing a heteroatom and having from 1 to about 20 carbon atoms, a hydrocarbon radical containing a heteroatom and having from 1 to about 20 carbon atoms, an aryl group containing a heteroatom, and an aryl group containing a heteroatom substituted by one or more alkyl groups.

3. The process of claim 2, wherein R$^2$ is selected from the group consisting of an alkyl group of from 1 to about 50 carbon atoms where the alkyl group can be straight or branched and substituted or unsubstituted, a carbamate, a benzyl group, an acyl group, a silyl group, an acid group, and a sulfonate group.

4. The process of claim 2, wherein the amine is an aniline.

5. The process of claim 2, wherein the amine is a diarylamine.

6. The process of claim 2, wherein the amine is a diphenylamine.

7. The process of claim 1, wherein the alcohol protecting agent is a methylating reagent.

8. The process of claim 1, wherein the alcohol protecting agent is selected from the group consisting of iodomethane, methyl chloride, methyl bromide, dimethyl sulfate, and dimethyl carbonate.

9. The process of claim 1, wherein the first base and second base are independently selected from bases represented by a general formula MOR, where:
   O is oxygen;
   M is a metal selected from the group consisting of potassium, sodium, lithium, calcium, magnesium; and
   R is a hydrogen or a straight or branched alkyl group selected from the group consisting of methyl, ethyl, propyl, butyl, pentyl, hexyl, heptyl, octyl, nonyl, and decyl groups.

10. The process of claim 1, wherein:
the first base is potassium hydroxide, and
the second base is selected from the group consisting of potassium tert-butoxide salt, sodium t-pentoxide, and sodium t-butoxide.

11. The process of claim 1, wherein the step (1) is carried out in a first solvent, and the step (2) is carried out in a second solvent different from said first solvent.

12. The process of claim 11, wherein the first solvent is a polar aprotic solvent.

13. The process of claim 1, wherein the process is carried out under an inert atmosphere.

14. The process of claim 1, wherein the step (1) is a Buchwald reaction.

15. The process of claim 1, wherein the catalyst is a palladium ligated catalyst.

16. The process of claim 1, wherein the catalyst is a palladium acetate ligated with a molecule given by structural formula (I):

wherein:
each X individually represents either CH$_2$ or an oxygen atom;

Y$^1$, Y$^2$, Y$^3$, and Y$^4$ each individually represent a substituted or unsubstituted, straight or branched, alkyl, alkenyl, or alkynyl group, having from 1 to about 10 carbon atoms; and Y$^5$ represents hydrogen, a substituted or unsubstituted alkyl group, or an aryl group.

17. The process of claim 16, wherein the molecule given by structural formula (I) is 2,4,6-trioxa-1,3,5,7-tetramethyl-8-phosphaadamantane.

18. The process of claim 1, wherein the step (1) is an Ullmann reaction.

19. The process of claim 18, wherein the second base is selected from the group consisting of alkali metal hydroxides, alkali metal carbonates, alkali metal phosphates, and alkali metal alkoxides.

20. The process of claim 18, wherein:
the second base is selected from the group consisting of lithium hydroxide, sodium hydroxide, potassium hydroxide, rubidium hydroxide, and cesium hydroxide, lithium carbonate, sodium carbonate, potassium carbonate, rubidium carbonate, and cesium carbonate, trilithium phosphate, trisodium phosphate, and tripotassium phosphate, sodium methoxide, sodium ethoxide, potassium methoxide, potassium ethoxide, lithium tert-butoxide, sodium tert-butoxide, and potassium tert-butoxide.

21. The process of claim 18, wherein the Ullmann reaction is a ligand-accelerated Ullmann reaction, and the step (2) is further conducted in the presence of a bidentate ligand.

22. The process of claim 21, wherein the bidentate ligand is of one of the following formulas:

wherein 0 or 1 of the carbon atoms are replaced with N, or wherein from 0 to 3 of the carbon atoms are replaced with N, or the compound is benzo-fused and 0 to 2 of the carbon atoms of the five-membered ring are replaced with N; and wherein:

X$^2$ is selected from Br or I;

R$^1$ is selected from H, Cl, F, Br, I, C$_{1-4}$ alkyl, C$_{1-4}$ alkoxy, C$_{1-4}$ alkylene-O—C$_{1-4}$ alkyl, NH$_2$, NH(C$_{1-4}$ alkyl), N(C$_{1-4}$ alkyl)$_2$, C$_{1-4}$ alkylene-NH$_2$, C$_{1-4}$ alkylene-NH (C$_{1-4}$ alkyl), C$_{1-4}$ alkylene-N(C$_{1-4}$ alkyl)$_2$, C$_{3-10}$ carbocycle substituted with 0-2 R$^3$, 5-6 membered heterocycle comprising carbon atoms and 1-4 heteroatoms selected from N, O, and S and substituted with 0-2 R$^3$;

R$^2$ is selected from H, Cl, F, Br, I, C$_{1-4}$ alkyl, C$_{1-4}$ alkoxy, C$_{1-4}$ alkylene-O—C$_{1-4}$ alkyl, NH$_2$, NH(C$_{1-4}$ alkyl), N(C$_{1-4}$ alkyl)$_2$, C$_{1-4}$ alkylene-NH$_2$, C$_{1-4}$ alkylene-NH (C$_{1-4}$ alkyl), C$_{1-4}$ alkylene-N(C$_{1-4}$ alkyl)$_2$, C$_{3-10}$ carbocycle substituted with 0-2 R$^3$, 5-6 membered heterocycle comprising carbon atoms and 1-4 heteroatoms selected from N, O, and S and substituted with 0-2 R$^3$;

R$^3$ is selected from Cl, F, Br, I, C$_{1-4}$ alkyl, C$_{1-4}$ alkoxy, C$_{1-4}$ alkylene-O—C$_{1-4}$ alkyl, NH$_2$, NH(C$_{1-4}$ alkyl), N(C$_{1-4}$ alkyl)$_2$, C$_{1-4}$ alkylene-NH$_2$, C$_{1-4}$ alkylene-NH(C$_{1-4}$ alkyl), C$_{1-4}$ alkylene-N(C$_{1-4}$ alkyl)$_2$, and NO$_2$;

r is 1 or 2; and, the bidentate ligand is a hydrolytically stabile ligand that ligates with Cu(I) and comprises two heteroatoms selected from N and O.

23. The process of claim 21, wherein the bidentate ligand is selected from the group consisting of tetramethylethylenediamine, 2,2'-dipyridyl, 8-hydroxyquinoline, 1,10-phenanthroline, 8-hydroxyquinoline, and 1,10-phenanthroline.

24. A process for forming a triarylamine compound, comprising:
(1) reacting 4-chlorobenzyl alcohol with a methylating reagent and a first base to form a halogenated arylether compound, and
(2) reacting the halogenated arylether compound with aniline in the presence of a suitable palladium catalyst and a second base.

25. The process of claim 24, wherein the first base is potassium hydroxide.

26. A process for forming a triarylamine compound, comprising:
(1) reacting 4-chlorobenzyl alcohol with a methylating reagent and a first base to form a halogenated arylether compound, and
(2) reacting the halogenated arylether compound with diphenylamine in the presence of a suitable palladium catalyst and a second base.

27. The process of claim 26, wherein the first base is potassium hydroxide.

* * * * *